United States Patent [19]
Schultz

[11] Patent Number: 5,960,795
[45] Date of Patent: Oct. 5, 1999

[54] WOUND COVERING DEVICE

[75] Inventor: Tod H. Schultz, Arlington, Tex.

[73] Assignee: Tecnol Medical Products, Inc., Fort Worth, Tex.

[21] Appl. No.: 08/858,015

[22] Filed: May 16, 1997

Related U.S. Application Data

[63] Continuation-in-part of application No. 08/544,146, Oct. 17, 1995, Pat. No. 5,630,430, which is a continuation-in-part of application No. 08/278,575, Jul. 20, 1994, Pat. No. 5,497, 788, which is a continuation of application No. 08/092,594, Jul. 16, 1993, abandoned.

[51] Int. Cl.$^6$ .................................................. A61F 13/00
[52] U.S. Cl. .............................. 128/888; 602/42; 602/43; 602/54
[58] Field of Search .................................. 128/846, 888; 602/41, 42, 43, 47, 52, 57

[56] References Cited

U.S. PATENT DOCUMENTS

| | | |
|---|---|---|
| D. 385,038 | 10/1997 | Shultz . |
| 1,644,508 | 10/1927 | Blake . |
| 3,645,835 | 2/1972 | Hodgson . |
| 3,918,446 | 11/1975 | Buttaravoli . |
| 4,096,863 | 6/1978 | Kaplan et al. . |
| 4,165,748 | 8/1979 | Johnson . |
| 4,275,721 | 6/1981 | Olson . |
| 4,450,845 | 5/1984 | Engel . |
| 4,583,976 | 4/1986 | Ferguson . |
| 4,598,004 | 7/1986 | Heinecke ................................. 428/40 |
| 4,600,001 | 7/1986 | Gilman .................................... 128/156 |
| 4,614,183 | 9/1986 | McCracken et al. . |
| 4,641,643 | 2/1987 | Greer . |
| 4,669,458 | 6/1987 | Abraham et al. . |
| 4,678,462 | 7/1987 | Vaillancourt . |
| 4,704,177 | 11/1987 | Vaillancourt . |
| 4,730,611 | 3/1988 | Lamb ...................................... 128/156 |
| 4,753,232 | 6/1988 | Ward ...................................... 128/156 |
| 4,815,457 | 3/1989 | Mazars et al. ........................... 128/155 |
| 4,838,868 | 6/1989 | Forgar et al. . |
| 4,875,896 | 10/1989 | Kurtz . |
| 4,898,587 | 2/1990 | Mera . |
| 4,907,599 | 3/1990 | Kum . |
| 4,917,112 | 4/1990 | Kalt . |
| 4,926,850 | 5/1990 | Lott et al. ................................ 128/155 |
| 5,000,172 | 3/1991 | Ward ...................................... 128/155 |
| 5,012,801 | 5/1991 | Feret . |
| 5,018,516 | 5/1991 | Gilman ................................... 128/155 |
| 5,025,783 | 6/1991 | Lamb ...................................... 128/156 |
| 5,092,323 | 3/1992 | Riedel et al. . |
| 5,116,324 | 5/1992 | Brierly et al. . |
| 5,127,423 | 7/1992 | Draeger . |
| 5,160,328 | 11/1992 | Cartmell . |
| 5,170,781 | 12/1992 | Loomis . |
| 5,181,914 | 1/1993 | Zook . |

(List continued on next page.)

OTHER PUBLICATIONS

"STERI–STRIP™ Wound Closure System" Surgical Division, 3M Healthcare, © 1992, 3 pages.

Mosby, "Alexander's Care of the Patient in Surgery," ©1995 Mosby–Year Book, Inc., 4 pages.

U.S. application No. 08/092,594 Inman et al., Filed Jul. 16, 1993, "Wound Closure Device for Viewing a Wound and Method", Abandoned.

*Primary Examiner*—Michael A. Brown
*Attorney, Agent, or Firm*—Dority & Manning, P.A.

[57] ABSTRACT

A covering device (10) for use in covering lacerations, wounds, incisions, insertions of medical devices and the like. The wound covering device includes a flexible hinge member (26) having a width approximately coextensive with the portion of the wound to be covered. The hinge member (26) having a first portion (32) connected at one end to a cover dressing (18), and a second portion (34) connected to a handle member (12). The hinge member (26) having adhesive layers (36, 38) applied in appropriate places to adhere the hinge member (26) to the cover dressing (18), and the hinge member (26) to the patient. Handle member (12) and a protective member (40) are arranged to cover the device so that the device can be handled and applied by a person wearing surgical gloves.

39 Claims, 7 Drawing Sheets

U.S. PATENT DOCUMENTS

| | | | |
|---|---|---|---|
| 5,183,664 | 2/1993 | Ansell | 424/445 |
| 5,197,493 | 3/1993 | Grier-Idris . | |
| 5,254,338 | 10/1993 | Sakai et al. | 424/78.35 |
| 5,263,970 | 11/1993 | Preller . | |
| 5,282,791 | 2/1994 | Lipton et al. . | |
| 5,306,504 | 4/1994 | Lorenz | 424/449 |
| 5,336,162 | 8/1994 | Ota . | |
| 5,336,219 | 8/1994 | Krantz . | |
| 5,415,627 | 5/1995 | Rasmussen et al. | 602/57 |
| 5,497,788 | 3/1996 | Inman et al. . | |
| 5,520,629 | 5/1996 | Heinecke et al. . | |

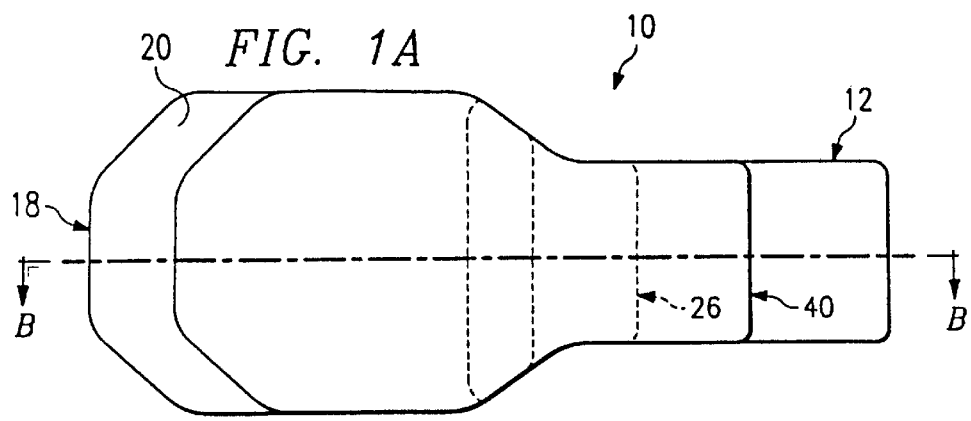
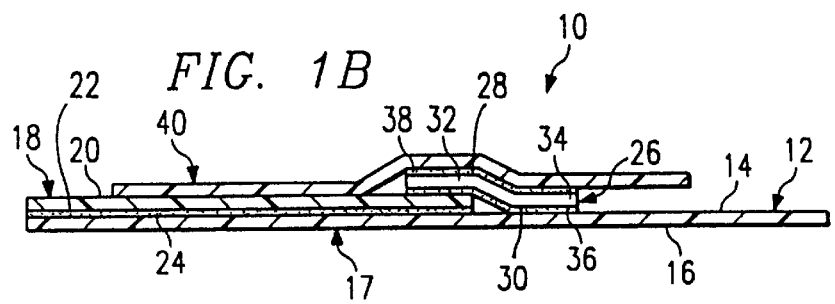
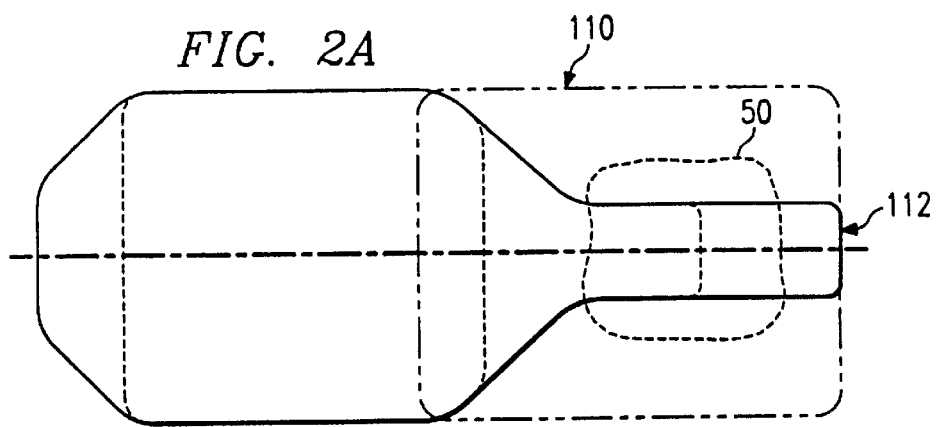
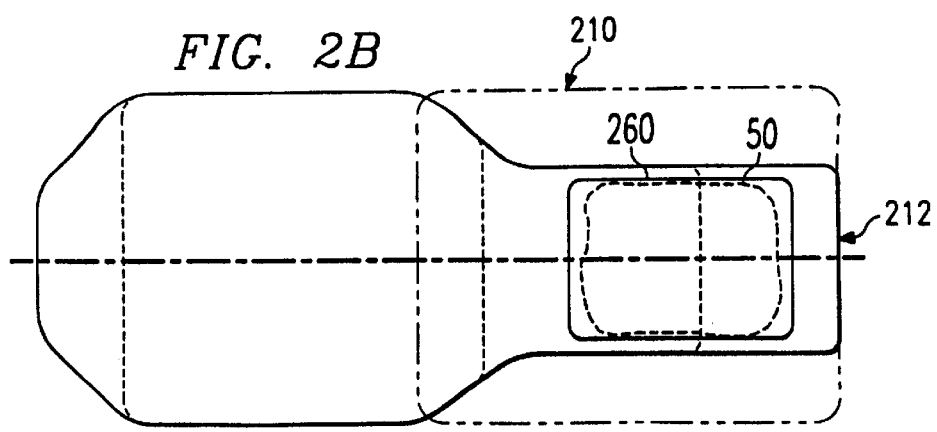

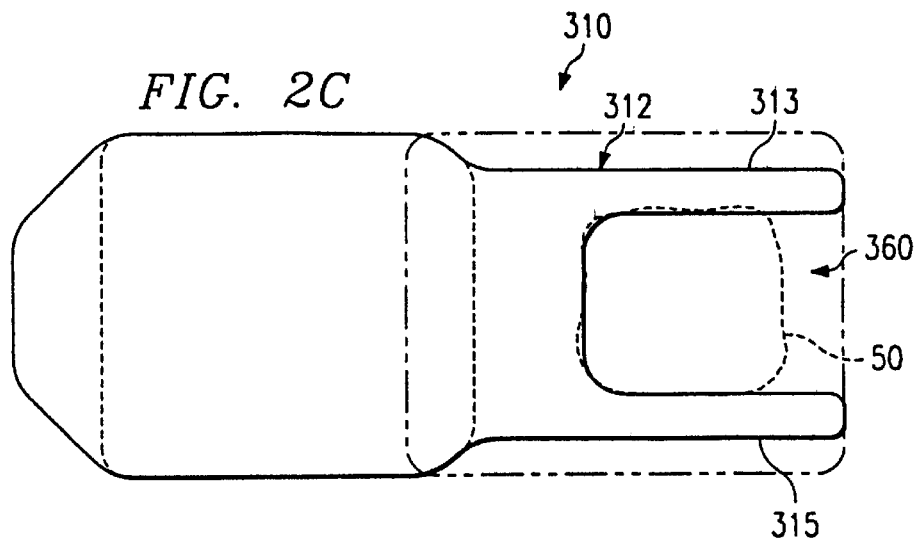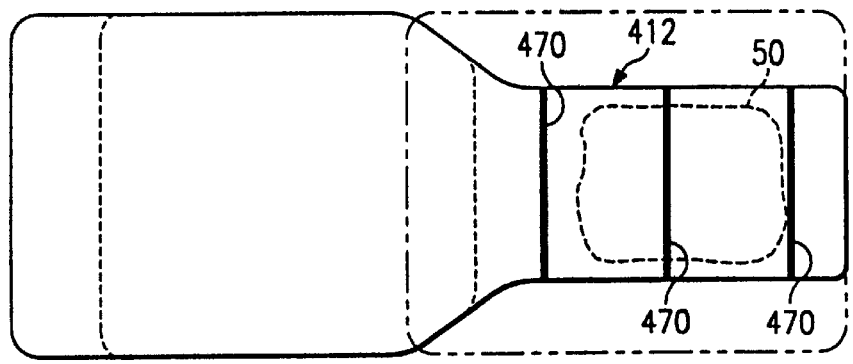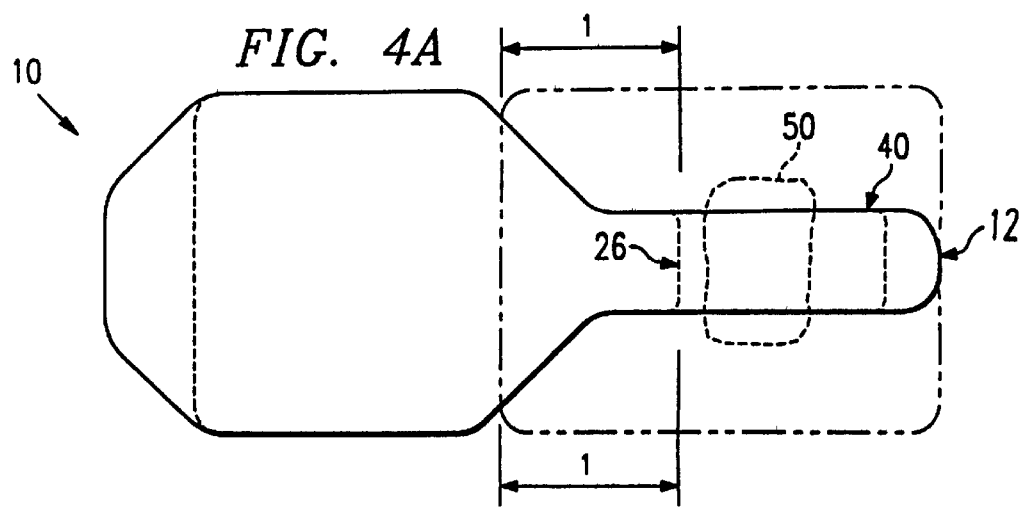

WOUND COVERING DEVICE

RELATED APPLICATIONS

This application is a continuation-in-part of application Ser. No. 08/544,146, filed Oct. 17, 1995, now U.S. Pat. No. 5,630,430 dated May 20, 1997, which is a continuation-in-part of application Ser. No. 08/278,575 filed Jul. 20, 1994, now U.S. Pat. No. 5,497,788 dated Mar. 12, 1996, which is a continuation of application Ser. No. 08/092,594 filed Jul. 16, 1993, now abandoned.

TECHNICAL FIELD OF THE INVENTION

This invention relates generally to devices for covering wounds, lacerations, incisions, inserted medical devices and the like. More particularly, but not by way of limitation, this invention relates to an improved device having one or more adhesive layers for covering wounds, lacerations, incisions, and inserted medical devices that can be easily applied by a person wearing surgical gloves and the like.

BACKGROUND OF THE INVENTION

The use of film dressings is well known for the purpose of covering wounds. Usually, such wounds are relatively small or are located in a position where there is little or no distension of the skin as a result of movement by the injured person. Wounds, incisions, lacerations, insertion of medical devices, and any related skin traumas wherein there is a separation or penetration of a patient's skin are interchangeable terms as used herein.

An example of a transparent film dressing is given by Robert W. McCracken, et al., in U.S. Pat. No. 4,614,183, issued on Sep. 30, 1986. The device is often difficult to apply when the user is wearing surgical gloves.

Another example of a transparent film dressing, which also includes a wound closure feature is embodied in a device sold under the trade name "Steri-Strip", Laparoscopic Wound Closure System featuring "Tegaderm" Transparent Dressing and made by the Medical-Surgical Division of 3M Health Care, and related to U.S. Pat. No. 3,645,835. When using this dressing, it appears that a narrow closure member is removed, or partially removed, from a release treated paper backing and applied to close the wound. It is then necessary to remove a very thin transparent film that is separate from the closure member and apply this film to cover the area of the trauma.

While this device may effectively cover the wound, it is often difficult to apply when wearing gloves.

U.S. Pat. No. 5,630,430 entitled *Wound Closure Device for Viewing a Wound* and U.S. Pat. No. 5,497,788 entitled *Wound Closure Device for Viewing a Wound and Method* disclose additional examples of transparent film dressings. Each of the above U.S. Patents are incorporated by reference for all purposes in this application.

SUMMARY OF THE INVENTION

In accordance with teachings of the present invention, an improved wound covering device is provided to substantially reduce or eliminate shortcomings previously associated with such wound covering devices.

According to one aspect of the present invention a wound covering device for covering and sealing at least a portion of a patient's wound includes an elongated handle member and a cover dressing which is releasably secured to the handle member by a first adhesive layer. The first adhesive layer may be used to secure the cover dressing to an area of skin adjacent to a patient's wound when the cover dressing is disposed in an overlying relation to the wound. The wound covering device further including a flexible hinge member having a width that is approximately coextensive with a portion of the wound to be covered. The flexible hinge member further having a first portion disposed on the cover dressing and a second portion disposed on the handle member. The first portion of the flexible hinge member preferably affixed to the cover dressing by a second adhesive layer. The wound covering device still further including a third adhesive layer disposed on a side of the flexible hinge member remote from the cover dressing for securing the flexible hinge member to the patient's skin adjacent to the wound.

According to another aspect of the present invention, a wound covering device may include a viewing portion in the handle member for facilitating alignment of the wound covering device relative to at least a portion of the wound to be covered.

According to yet another aspect of the present invention, a wound covering device includes a primary dressing disposed on the second portion of the hinge member.

BRIEF DESCRIPTION OF THE DRAWINGS

For a more complete understanding of the present invention, and the advantages thereof, reference is now made to the following written description taken in conjunction with the accompanying drawings in which like reference numbers indicate like features, and wherein:

FIG. 1A is a top view of a wound covering device constructed in accordance with teachings of the present invention;

FIG. 1B is a sectional view of the wound covering device of FIG. 1A taken generally along line B—B of FIG. 1A;

FIG. 2A is a top view of a wound covering device showing the associated handle member disposed over a wound;

FIG. 2B is a top view of another embodiment of a wound covering device showing the associated handle member disposed over a wound;

FIG. 2C is a top view of yet another embodiment of a wound covering device showing the associated handle member disposed over a wound;

FIG. 3 is a top view of a wound covering device showing the associated handle member having an alignment pattern;

FIGS. 4A–4D are schematic drawings showing an exemplary method of applying a wound covering device according to teachings of the present invention;

DETAILED DESCRIPTION OF THE INVENTION

Figure 1C:
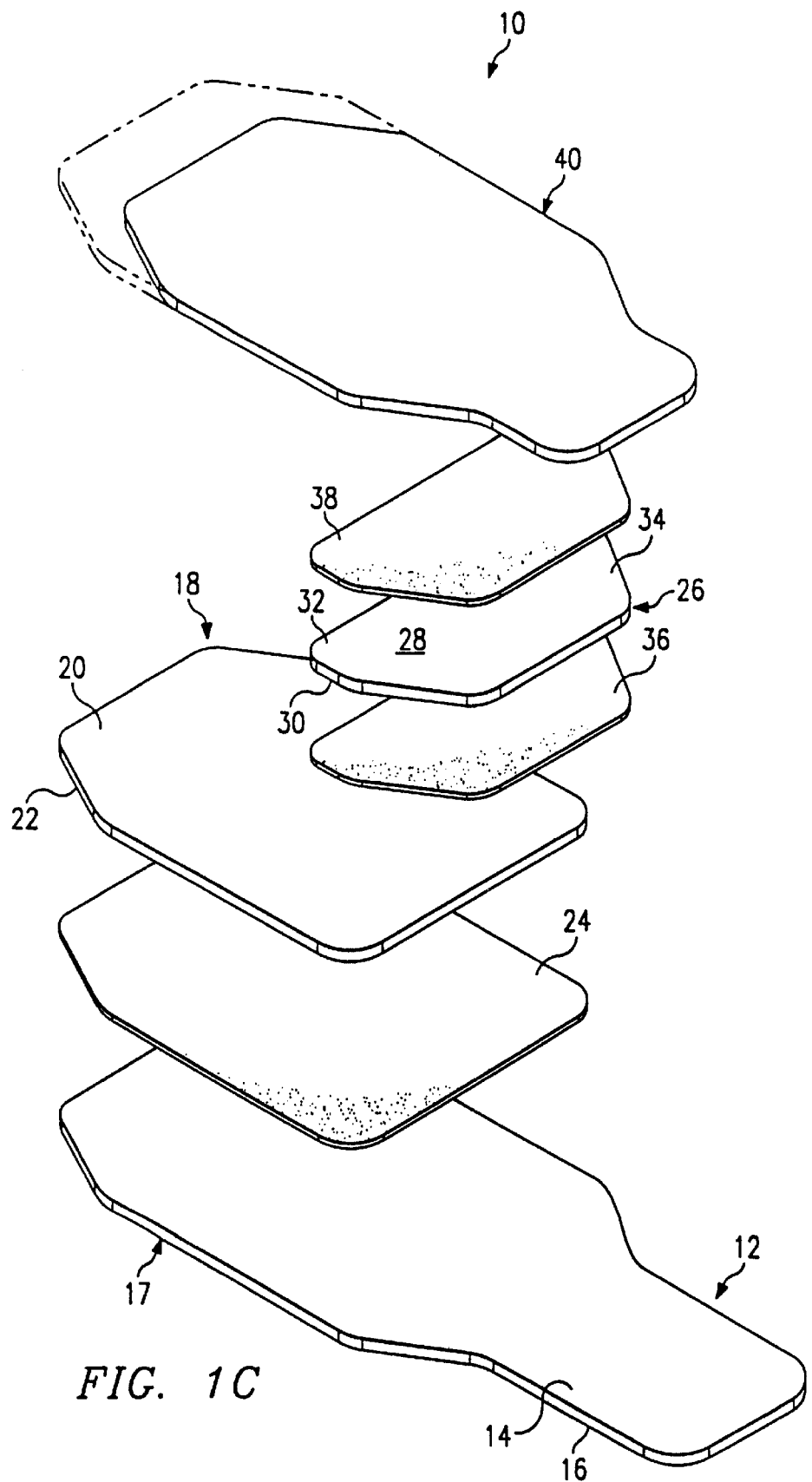
FIG. 1C is an exploded view of the wound closure device of FIG. 1A.

The preferred embodiments of the present invention and its advantages are best understood by referring to FIGS. 1–9 of the drawings, like numerals being used for like and corresponding parts of the various drawings. It will be understood that the thicknesses of the layers of materials and other dimensions in the drawings have been greatly exaggerated for purposes of illustration.

FIGS. 1A–1C show various views of a wound covering device 10. Wound covering device 10 includes elongated handle member 12, which has first side 14 and second side 16. Wound covering device 10 further includes cover dressing 18 having first side 20 and second side 22. First adhesive layer 24 may be disposed on first side 22 of cover dressing 18 such that adhesive layer 24 resides between first side 22 of cover dressing 18 and first side 14 of handle member 12. Wound covering device 10 may also include flexible hinge member 26 having first side 28 and second side 30. Hinge member 26 preferably has a width that is approximately coextensive with a portion of the wound to be covered by wound covering device 10. Hinge member 26 may further include first portion 32 and second portion 34. Second adhesive layer 36 may be disposed on second side 30 of first hinge member 26. For the embodiment shown in FIGS. 1B and 1C, second adhesive layer 36 extends over second side 30 of first portion 32 and second portion 34. For some applications, second adhesive layer 36 may only be disposed on second side 30 corresponding with first portion 32.

Third adhesive layer 38 may further be disposed on first side 28 of hinge member 26. First portion 32 of hinge member 26 is disposed on cover dressing 18 such that second adhesive layer 36 resides between cover dressing 18 and hinge member 26. Second portion 34 of hinge member 26 is disposed on first side 14 of handle member 12. Second adhesive layer 36 may or may not reside between first portion 32 of hinge member 26 and side 14 of handle member 12. Protective member 40 may be disposed on third adhesive layer 38. Protective member 40 may extend beyond first portion 32 of hinge member 26 to cover some or all of first side 20 of cover dressing 18. Similarly, protective member 40 may extend beyond second portion 34 of hinge member 26 to cover some or all of first side 14 of handle member 12.

Handle member 12 preferably includes an enlarged portion 17 that is at least coextensive with cover dressing 18 so as to prevent undesired exposure of first adhesive layer 24. Provided a portion of handle member 12 is at least coextensive with first adhesive layer 24, handle member 12 may take any size and shape appropriate for a particular application. Handle member 12 may be transparent or opaque, and may be formed from a variety of materials, such as paper, polyester, polyethylene or laminates of these materials. In addition, handle member 12 may be silicon coated on first side 14 to facilitate easy release from cover dressing 18.

First adhesive layer 24 operates to adhere second side 22 of cover dressing 18 to a patient's skin surrounding a wound. To accomplish this objective, first adhesive layer 24 may, but need not be coextensive with second side 22 of cover dressing 18. First adhesive layer 24 may occupy any area of cover dressing 18 suitable to create an adequate bond between cover dressing 18 and the skin surrounding the wound. For example, first adhesive layer 24 may be located in a relatively narrow band around the periphery of cover dressing 18. To assist in the healing process, adhesive layer 24 may be impregnated with a variety of medicinal agents, such as antimicrobial compounds, antifungal compounds and/or antibacterial compounds. First adhesive layer 24 further operates to releasably attach first side 14 of handle member 12 to second side 22 of cover dressing 18. A release coating may be applied to first side 14 of handle member 12 so that handle member 12 can be readily separated from cover dressing 18 despite the presence of adhesive layer 24.

Cover dressing 18 operates to cover at least a portion of the wound to be covered. Where cover dressing 18 is coextensive with or larger than the wound to be covered, cover dressing 18 may be used to cover the entire wound. In cases where cover dressing 18 is smaller than the area to be covered, multiple wound covering devices may be used to cover the entire wound. Cover dressing 18 may be fashioned in any shape, size and configuration appropriate to specific applications.

When disposed in an overlying relation to the wound, cover dressing 18 preferably forms a barrier around the portion of the wound covered. This barrier may prevent external contaminants from entering the wound site, and may also prevent wound exudates from leaking from the wound site. Cover dressing 18 may be transparent or opaque. Utilizing a transparent cover dressing is advantageous in that it facilitates observation of the wound throughout the healing process. Cover dressing 18 may be formed from a variety of materials, such as polyethylene, polyurethane, polypropylene, polyester, woven or non-woven substrates or hydrogel. Depending on the application, cover dressing 18 may comprise a hydrophobic material or a hydrophilic material. To further assist the healing process, cover dressing 18 may be loaded with one or more medicinal agents, such as antimicrobial compounds, antifungal compounds, and/or antibiotic compounds.

Hinge member 26 operates to secure wound covering device 10 to a selected location or locations adjacent to a patient's wound. Hinge member 26 preferably has a width that is approximately coextensive with the portion of the wound to be covered by cover dressing 18. It should be noted that hinge member 26 need not be exactly coextensive with the portion of the wound to be covered. Hinge member 26 may be somewhat smaller or larger than the portion of the wound to be covered without departing from the spirit of the invention. In addition, hinge member 26 may be any length. In some applications a primary dressing (not shown) may be affixed to hinge member 26 and subsequently aligned over a portion of the wound to be covered. Details of affixing and utilizing a primary dressing are described below. Hinge member 26 may be transparent or opaque and may be formed from a variety of materials including polyethylene, polyurethane, polyester, woven substrates, non-woven substrates, hydrogel or foam. To further assist in the healing process, hinge member 26 may be loaded with one or more medicinal agents, such as antimicrobial compounds, antifungal compounds, and/or an antibiotic compounds. Details of the function of hinge member 26 are described below.

Second adhesive layer 36 serves to connect first side 20 of cover dressing 18 with second side 30 of first portion 32 of hinge member 26. Second adhesive layer 36 may be disposed on first side 20 of cover dressing 18, or on second side 30 of first portion 32 of hinge member 26. Second adhesive layer 36 may occupy any portion of first side 20 of cover dressing 18 or second side 30 of first portion 32 of hinge member 26 suitable to create a bond between the two structures. Second adhesive layer 36 may, but need not reside between handle member 12 and second side 30 of second portion 34 of hinge member 26.

Third adhesive layer 38 may cover both first portion 32 and second portion 34 of first side 28 of hinge member 26. Third adhesive layer 38 serves to bond first side 28 of hinge member 26 to a selected area of skin adjacent to a patient's wound. Third adhesive layer 38 may occupy any area of first side 28 of hinge member 26 suitable to create an effective bond between first side 28 of hinge member 26 and the selected area of the patient's skin adjacent to a wound. To assist in the healing process, third adhesive layer 38 may be impregnated with a variety of medicinal agents, such as antimicrobial compounds, antifungal compounds and/or antibacterial compounds.

It should be observed that when the care giver peels handle member 12 away from second portion 34 of hinge member 26, any adhesive residing between handle member 12 and second portion 34 of hinge member 26 may tend cause hinge member 26 to be peeled away from the patient's skin. To ensure that hinge member 26 is not removed from the patient's skin when handle member 12 is peeled away, it may be advantageous to leave part of second side 30 of second portion 34 of hinge member 26 free from adhesive. For example, an area of second side 30 of second portion 34 of hinge member 26 remote from cover dressing 18 may be left free from second adhesive layer 36. In this way, third adhesive layer 38 may form a primary bond between hinge member 26 and the patient's skin, while second adhesive layer 36 forms a weaker secondary bond between handle member 12 and second portion 34 of hinge member 26. The care give away then peel handle member 12 may from second portion 34 of hinge member 26 without removing hinge member 26 from the patient's skin adjacent to the wound.

Protective member 40 is preferably releasably attached to hinge member 26 by third adhesive layer 38. A release coating may be applied to the side of protective member 40 adjacent to third adhesive layer 38 so that protective member 40 can be easily separated from hinge member 26 despite the presence of third adhesive layer 38. Protective member 40 is at least coextensive with third adhesive layer 38 so as to prevent undesired exposure of third adhesive layer 38 prior to its application to a patient's skin. Provided that protective member 40 is at least coextensive with third adhesive layer 38, it may take any size and shape. Protective layer 40 may be advantageously fashioned to have dimensions different from those of handle member 12 so that protective member 40 can be readily removed from hinge member 26 when wound covering device 10 is to be applied to the patient's skin adjacent to the wound. Protective member 40 may be formed from a variety of materials, such as paper, polyester, polyethylene, or laminates of these materials.

FIGS. 2A–2C illustrate various embodiments of wound covering devices 110, 210 and 310, respectively, as well as a method of aligning the wound covering device over a wound according to teachings of the present invention. FIGS. 2A–2C illustrate that elongated handle members 112, 212 and 312 may take a variety of shapes and sizes. In one embodiment (FIG. 2A) handle member 112 may cover an area smaller than a portion of wound 50 to be covered. In such a case, a care giver may align wound covering device 110 by placing handle member 112 in a position approximately over the center of the portion of wound 50 to be covered. In another embodiment (FIG. 2B) handle member 212 may include viewing portion 260. Viewing portion 260 may comprise any portion, or all of handle member 212. In one embodiment, viewing portion 260 includes the entirety of handle member 212, which may be formed from a substantially transparent material to facilitate observation of wound 50 during alignment of wound covering device 210. In another embodiment, viewing portion 260 may comprise only a part of handle member 212. In such a case, viewing portion 260 may comprise a substantially transparent portion of an otherwise opaque handle member. In still another embodiment, viewing portion 260 may consist of an excised portion of handle member 212 through which all or part of wound 50 is visible. Handle member 212 may be die cut to any shape to form viewing portion 260.

FIG. 2C illustrates still another embodiment in which handle member 312 includes viewing portion 360 which has been die cut to suit a particular application. In this case, handle member 312 may include a first prong 313 and a second prong 315. Prongs 313 and 315 may be die cut to any size, shape or configuration suitable to a particular application. The configuration of handle member 312 may be useful in applications such as where a large dressing requires two hands to deliver the dressing to the wound site.

FIG. 3 illustrates a wound covering device 410 in which elongated handle member 412 includes alignment pattern 470 for aiding in placement of wound covering device 410 over wound 50. Although alignment pattern 470 is shown as three parallel lines, it should be noted that alignment pattern 470 could be any desired pattern helpful in aiding the care giver to align wound covering device 410 over wound 50. For example, alignment pattern 470 may be a single line, several offset lines, a centering point or a grid pattern. In addition to aiding the care giver in positioning wound covering device 410 over wound 50, alignment pattern 470 may be used to align wound covering device 410 over a medical device, such as a catheter or intravenous tube extending from the patient's skin.

FIGS. 4A–4D illustrate a method of applying a wound covering device 10 according to the teachings of the present invention. A care giver 100 begins the method of applying wound covering device 10 by removing wound covering device 10 from a sterile package (not shown) Upon removing wound covering device from its packaging, there is no live adhesive exposed. Care giver 100 proceeds by grasping handle member 12 and cover dressing 18, and removing protective member 40 to expose adhesive layer 38. Because there is no adhesive on the side 16 of handle member 12 or side 20 of cover dressing 18, care giver 100 may grasp wound covering device 10 without sticking to it. Care giver 100 may dispose of protective member 40, or alternatively, may sketch or write notes on protective member 40 and retain it for future reference.

Care giver 100 may next align handle member 12 over a wound 50 to be covered (FIG. 4A). Care giver 100 may be aided in aligning the handle member by viewing portion 260 or 360 and/or alignment pattern 470 (FIGS. 2B, 2C and 3). If the wound covering device is used to cover and/or secure a medical device extending from a patient's skin, the care giver will begin by aligning the medical device with an alignment pattern on the handle member. In that type of application, the present invention provides an advantage of enabling the care giver to apply the wound covering device with one hand while holding the medical device secure with the other.

Figure 4B:
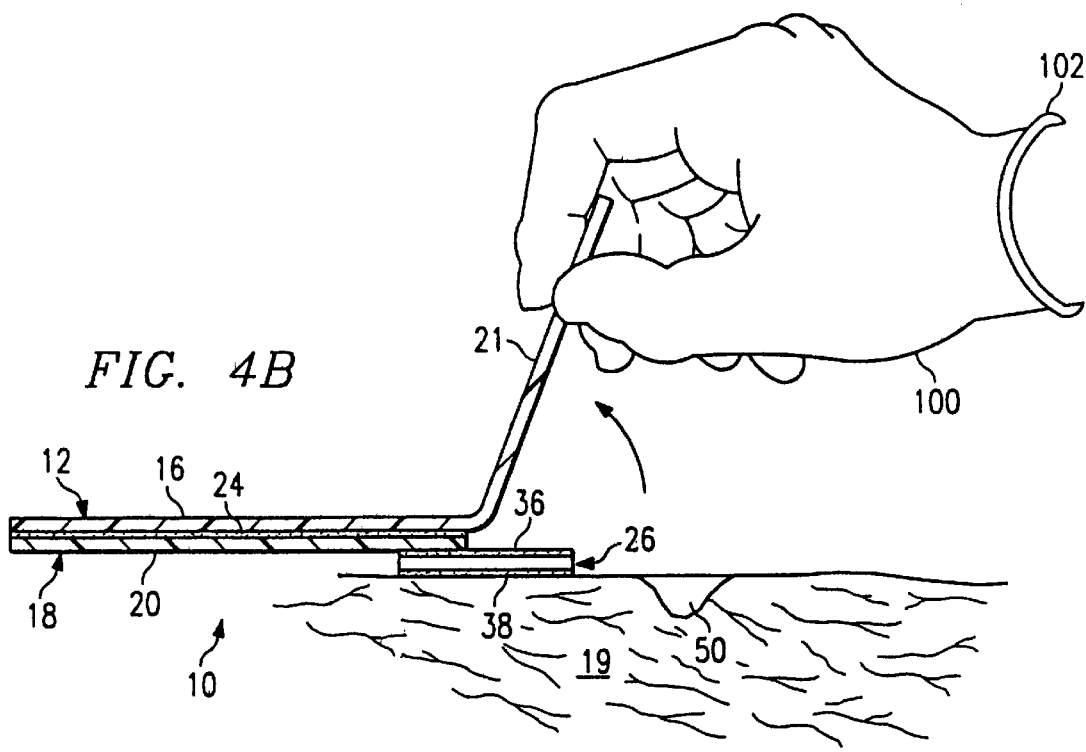
Figure 4C:
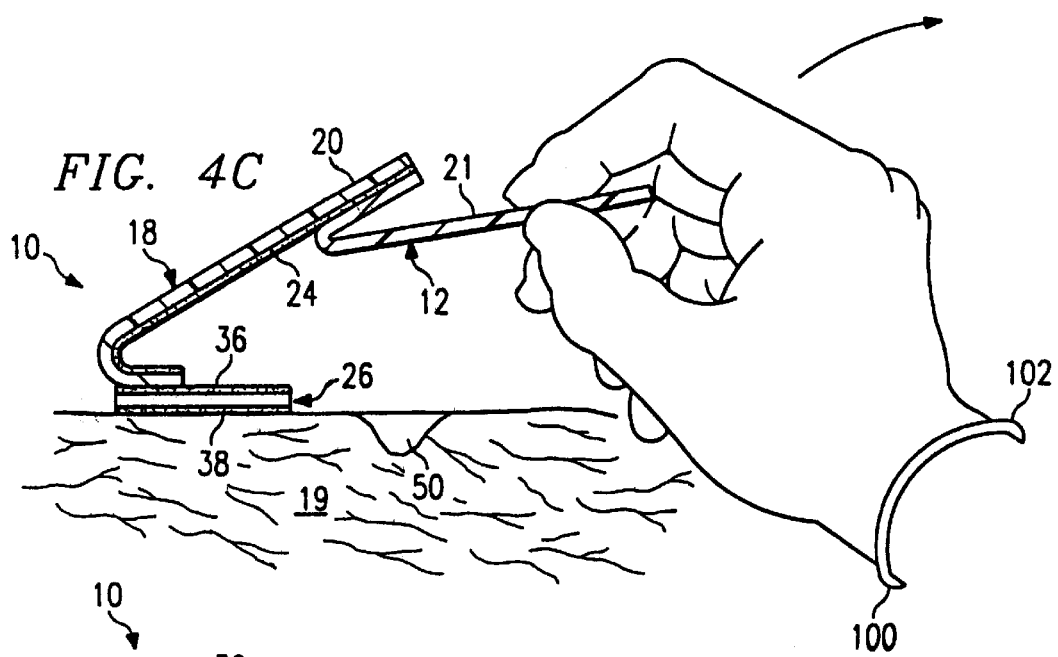

Once wound covering device 10 is properly aligned, care giver 100 may apply pressure across area 1—1 to affix hinge member 26 to a patient's skin 19 adjacent to the portion of the wound to be covered. This causes wound covering device 10 to be affixed to the patient's skin in a location selected by care giver 100. Care giver 100 may next grasp handle member 12 at an area 21 remote from cover member 18, and peel handle member 12 away from hinge member 26 until cover dressing 18 is encountered (FIG. 4B). Upon encountering cover dressing 18, care giver 100 peels handle member 12 away from cover dressing 18, drawing cover dressing 18 over wound 50 (FIG. 4C) Care giver 100 continues to peel handle member 12 from cover dressing 18 until cover dressing 18 overlies the wound and handle member 12 separates from cover dressing 18. Once handle member 12 has separated from cover dressing 18, care giver 100 may write notes, such as the date of the application of wound covering device 10, on handle member 12, and retain handle member 12 in the patient's records for future reference. Additionally, care giver 100 may sketch the outline of wound 50 on handle member 12 to make a record of the extent of the wound for future reference.

Figure 4D:
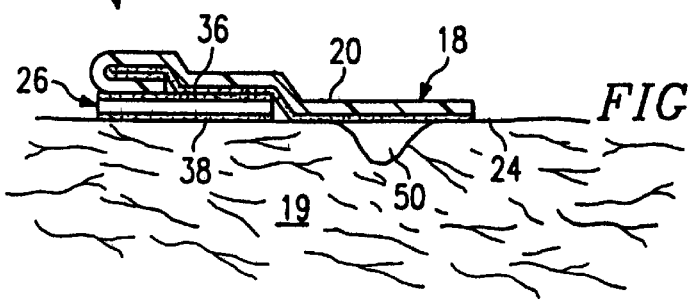

Once cover dressing 18 is disposed in an overlying relationship to wound 50, care giver 100 may apply pressure to cover member 18 to affix it securely to the skin surrounding wound 50 (FIG. 4D). Cover member 18 forms a barrier around wound 50. This barrier may prevent external contaminants from entering the wound site, and may also prevent wound exudates from leaking from the wound site. In the case of application of wound covering device 10 to a medical device extending from the patient's skin, cover dressing 18 secures the position of the medical device and forms a similar barrier around the medical device.

Figure 5A:
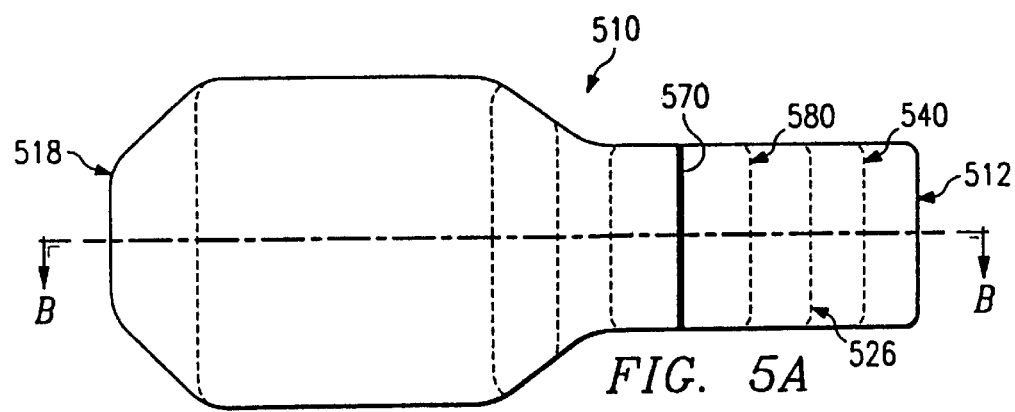
FIG. 5A is a top view of another embodiment of a wound covering device according to the teachings of the present invention.
Figure 5B:
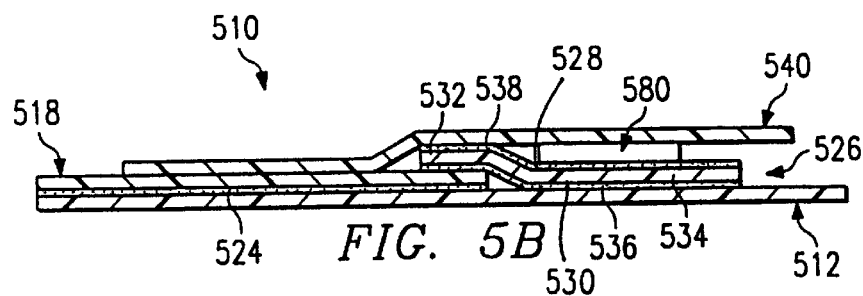
FIG. 5B is a drawing in section of the wound covering device shown in FIG. 5A taken generally along the line B—B.

FIGS. 5A and 5B show a top view and a cross-sectional view, respectively, of another embodiment of a wound covering device according to the teachings of the present invention. Wound covering device 510 is structurally similar to wound covering device 10 shown in FIGS. 1A–1C. Wound covering device 510 includes handle member 512, which is similar in structure and function to handle member 12 of FIGS. 1A–1C. Like handle member 412 shown in FIG. 3, handle member 512 may include an alignment pattern 570 for aiding in the alignment of wound covering device 510 over a wound. Alignment pattern 570 may be a variety of patterns, such as a single line, a set of parallel lines, a centering point or a grid pattern. Wound covering device 510 further includes a cover dressing 518 disposed on handle member 512. Cover dressing 518 is similar in structure and function to cover dressing 18 of FIGS. 1A–1C. A first adhesive layer 524, which is disposed on cover dressing 518, is similar in structure and function to adhesive layer 24 in FIGS. 1A–1C.

Wound covering device 510 further includes a flexible hinge member 526 having a first side 528 and a second side 530. Hinge member may further include a first portion 532 and a second portion 534. First portion 532 of hinge member 526 is disposed on cover dressing 518. A second adhesive layer 536 may reside between first portion 532 of hinge member 526 and cover dressing 518. Adhesive layer 536 may be disposed on cover dressing 18 or second side 530 of first portion 532 of hinge member 526. Adhesive layer 536 may occupy any portion of cover dressing 518 or first portion 532 of hinge member 526 suitable to create a bond between the two structures. Second portion 534 of hinge member 526 may be disposed on handle member 512. Adhesive layer 536 may or may not reside between handle member 512 and second portion 534 of hinge member 526. As previously described in reference to wound covering device 10, it may be advantageous to leave a part of second portion 534 of hinge member 526 free from second adhesive layer 536, thus avoiding separation of hinge member 526 from the patient's skin when handle member 512 is removed. First portion 532 of hinge member 526 is similar in structure and function to first portion 32 of hinge member 26 in FIGS. 1A–1C. Second portion 534 of hinge member 526 may be elongated to support a primary dressing 580 disposed on first side 528 of second portion 534 of hinge member 526. Wound covering device 510 may include primary dressing 580. If wound covering device 510 does not already include primary dressing 580, a care giver may affix a primary dressing to hinge member 526.

A third adhesive layer 538 is disposed on at least a portion of hinge member 526 on first side 28 of hinge member 526 remote from handle member 512. Adhesive layer 538 serves to bond the side of hinge member 526 remote from handle member 512 to an area of skin adjacent to a patient's wound. Adhesive layer 538 may occupy any area of the side of hinge member 526 remote from handle member 512 suitable to create an effective bond between hinge member 526 and an area of the patient's skin adjacent to a wound. Adhesive layer 538 may further function to adhere primary dressing 580 to first side 528 of second portion 534 of hinge member 526. Alternatively, primary dressing 580 may include its own adhesive layer (not shown) facilitating a bond between a primary dressing 580 and first side 528 of second portion 534 of hinge member 526. Second portion 534 of hinge member 526 and adhesive layer 538 may extend beyond the perimeters of primary dressing 580. In this way, primary dressing 580 may be disposed on a patient's wound and secured in place by affixing hinge member 526 on the patient's skin adjacent to the wound on either side of the wound.

Primary dressing 580 may be formed from a variety of materials including foam, hydrogel, hydrocolloid, silicon, woven substrates, non-woven substrates or alginate. Depending on the application, primary dressing 580 may be hydrophobic or hydrophilic. Similarly, depending on the application, primary dressing 580 may be loaded with medicinal agents such as antimicrobial compounds, antifungal compounds and/or antibacterial compounds to reduce the risk of infection.

A protective member 540 may be releasably attached to hinge member 526 by adhesive layer 538. A release coating may be applied to the side of protective member 540, adjacent to adhesive layer 538 so that protective member 540 can be easily separated from hinge member 526 despite the presence of adhesive layer 538. Protective member 540 is at least co-extensive with adhesive layer 538 so as to prevent undesired exposure of adhesive layer 538 prior to its application to a patient's skin. Provided that protective member 540 is at least co-extensive with adhesive layer 538, it may take any size, shape and configuration. Protective layer 540 may be advantageously fashioned to have dimensions different from those of handle member 512, so that protective member 540 can be readily removed from hinge member 526 when the device is to be applied to the patient's skin adjacent to the wound. Protective member 40 may be formed from a variety of materials, such as paper, polyester, polyethylene or laminates of these materials. Care givers may sketch or write notes on protective member 40 and retain protective member 540 for future reference.

Figure 6:
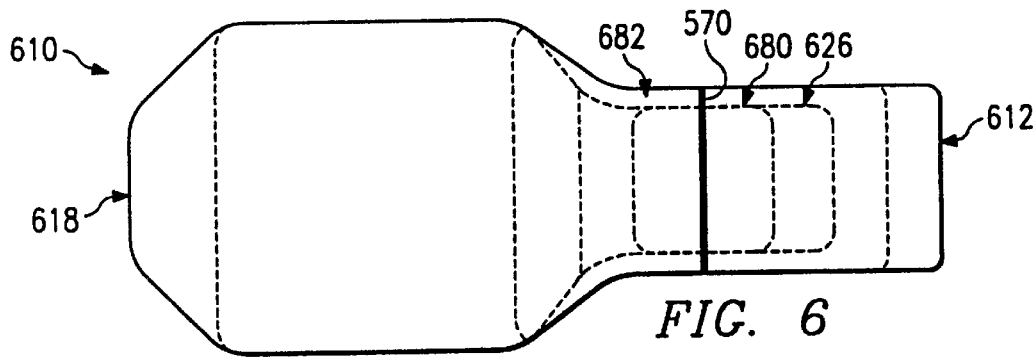
FIG. 6 is a schematic drawing showing a top view of a modified version of the wound covering device shown in FIG. 5A.

FIG. 6 shows a top view of another embodiment of a wound covering device 610 according to the teachings of the present invention. Although all the components are not shown in FIG. 6, the wound covering device 610 includes the same structural components as did the device 510 described in detail hereinbefore. The modification of FIG. 6, as compared to the wound covering device 510, resides in a change to the configuration of a hinge member 526 and a primary dressing 680. While hinge member 526 and primary dressing 580 extend to meet the perimeter of handle member 512, the perimeters of hinge member 626 and primary dressing 680 have been excised, or kiss-cut, to form a dry edge 682 around a portion of the perimeters of hinge member 626 and primary dressing 680. Dry edge 682 protects against cold flow causing live adhesive to flow beyond the perimeters of handle member 512 and protective member 540. Because there is an adhesive layer between hinge member 626 and primary dressing 680, pressure applied to primary dressing 580 during shipping or handling may force the adhesive layer between the two to flow beyond the perimeters of these structures. The resulting live adhesive could cause difficulties if it were to contact packaging materials around wound covering device 610. Further, such live adhesive reduces an advantage of this invention; providing a wound covering device which is easy to apply, even when a care giver is wearing Latex gloves. By excising a portion of the perimeters of hinge member 626 and primary dressing 680, dry edge 682 may be formed. Dry edge 682 becomes a protective area, guarding against cold flow of adhesive from the perimeters of hinge member 626 and primary dressing 680.

Figure 7A:
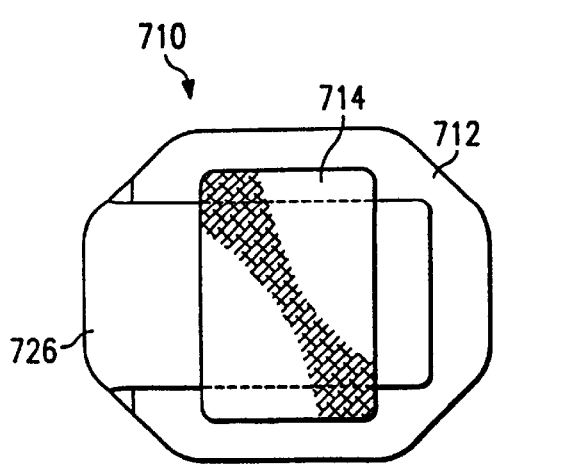
FIGS. 7A–7C are schematic drawings showing plan views of various embodiments of a wound covering device constructed according to teachings of the present invention.
Figure 7B:
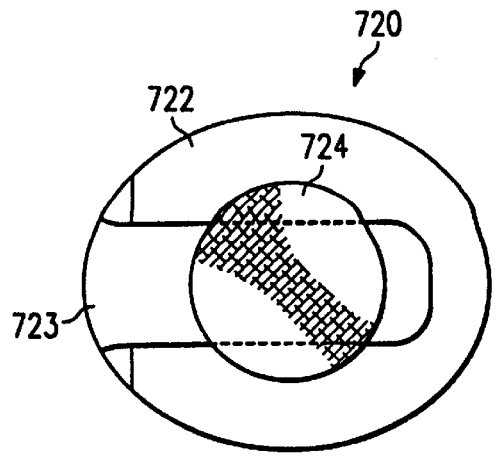
Figure 7C:
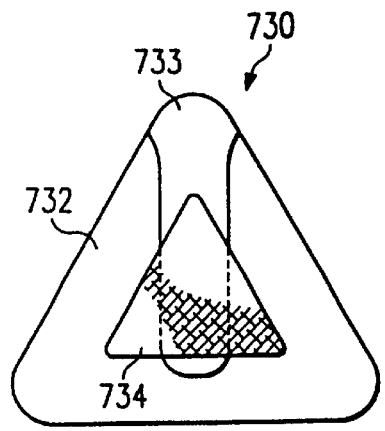

FIGS. 7A–7C illustrate various embodiments of wound covering devices according to teachings of the present invention. As shown, the hinge member, primary dressing and cover dressing may assume a variety of shapes, sizes and configurations depending on the application. The primary dressing may be any size relative to the hinge member. The cover dressing will generally be larger than the primary dressing to facilitate covering both the wound and the primary dressing and creating a seal around the portion of the wound to be covered.

FIG. 7A shows wound covering device 710 having hinge member 726, cover dressing 712 and primary dressing 714. Cover dressing 712 exhibits an octagonal shape and primary dressing 714 is rectangular. This configuration may be useful in a variety of applications. FIG. 7B shows a wound covering device 720 having a hinge member 723, an elliptical cover dressing 722 and a circular primary dressing 724. Wound covering device 720 may be advantageously applied to specific applications, such as covering pressure sores on a patient's hip, ankle, shoulder, elbow or heel. FIG. 7C illustrates a wound covering device 730 having hinge member 733, cover dressing 732 and primary dressing 734. Both cover dressing 732 and a primary dressing 734 exhibit a triangular shape. This configuration may be useful, for example, in an applications to pressure sores in the sacral-coccyx area.

Figure 8:
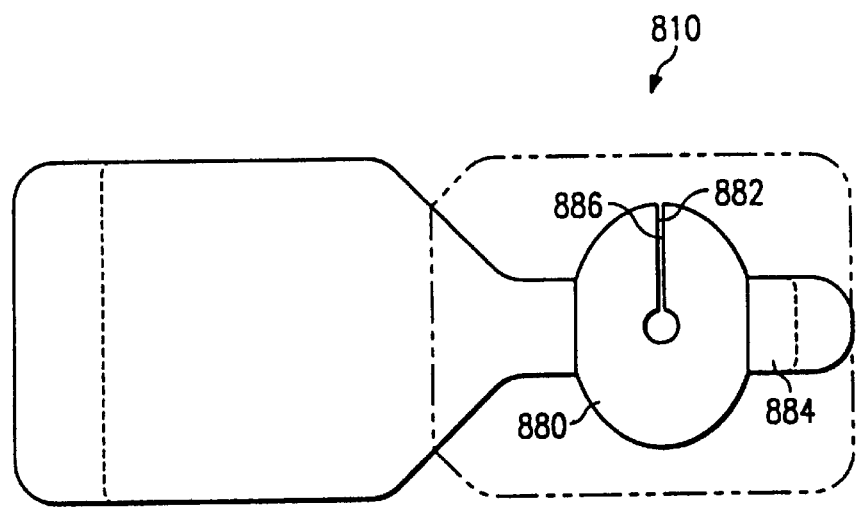
FIG. 8 is a schematic drawing showing a top view of still another embodiment of a wound covering device constructed according to teachings of the present invention.

FIG. 8 illustrates another embodiment of a wound covering device 810 in which a primary dressing 880 includes a first fenestration 882. Wound covering device 810 further includes a hinge member 884 having a second fenestration 886 corresponding to first fenestration 882 in primary dressing 880. Fenestration 882 and 886 facilitate placement of wound covering device 810 over a medical device such as a catheter or intravenous device extending from a patient's skin. In such applications, wound covering device 810 may serve to secure the medical device as well as to seal the skin around the medical device preventing moisture from escaping. Details of the application of wound covering device 810 to a medical device extending from a patient's skin are described below.

FIGS. 9A–9D show a method of applying a wound covering device according to the teachings of the present invention. A care giver 200 begins the method of applying wound covering device 510 by removing wound covering device 510 from a sterile package (not shown). Upon removing wound covering device from its packaging, there is no live adhesive exposed. Care giver 200 proceeds by grasping handle member 512 and cover dressing 518, and removing protective member 540 to expose adhesive layer 538 and primary dressing 580. Because there is no adhesive on the side of cover dressing 518 being grasped, wound covering device 510 will not stick to care giver 200. Care giver 200 may either dispose of protective member 540 or sketch or write notes on protective member 540 and retain it for future reference.

Figure 9A:
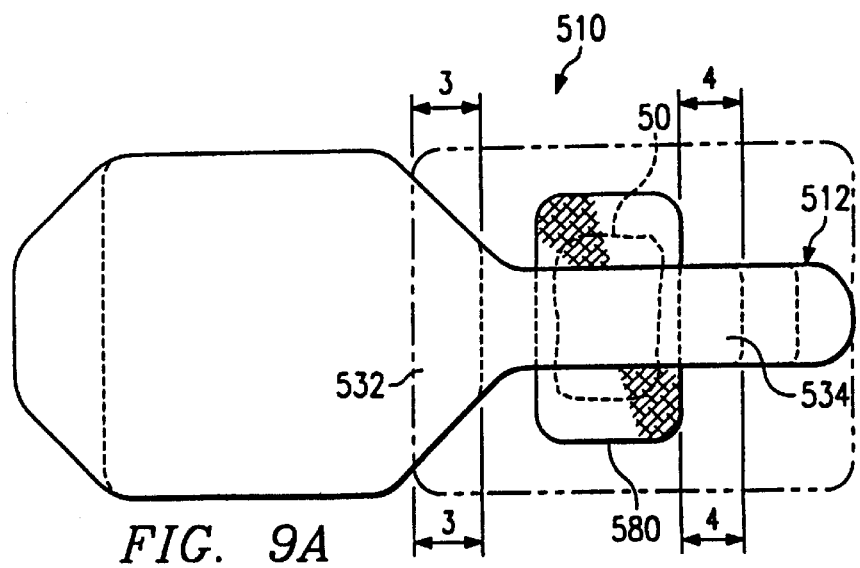
FIG. 9A–9D are schematic drawings showing an exemplary method of applying a wound covering device according to teachings of the present invention.

If wound covering device 510 does not already include a primary dressing, care giver 200 may affix primary dressing 580 to second portion 534 of hinge member 526 adjacent first side 528 of hinge member 526. Care giver 200 may next align primary dressing 580 over a wound 50 to be covered (FIG. 9A). If wound covering device 810 (FIG. 8) is used to cover and/or secure a medical device extending from a patient's skin, the care giver will begin by aligning the medical device with fenestrations 882 and 886 in primary dressing 880 and hinge member 884, respectively (FIG. 8). In that application, wound covering device 810 provides an advantage of enabling the care giver to apply wound covering device 810 with one hand while holding the medical device secure with the other.

Once wound covering device 510 is properly aligned, care giver 200 may apply pressure across area 3—3 to affix first portion 532 of hinge member 526 to a patient's skin adjacent to the wound to be covered. Depending on the configuration of the wound covering device, care giver 100 may or may not apply pressure over an area 4—4 to affix second portion 534 of hinge member 526 to an area of skin 95 adjacent to wound 50.

Figure 9B:
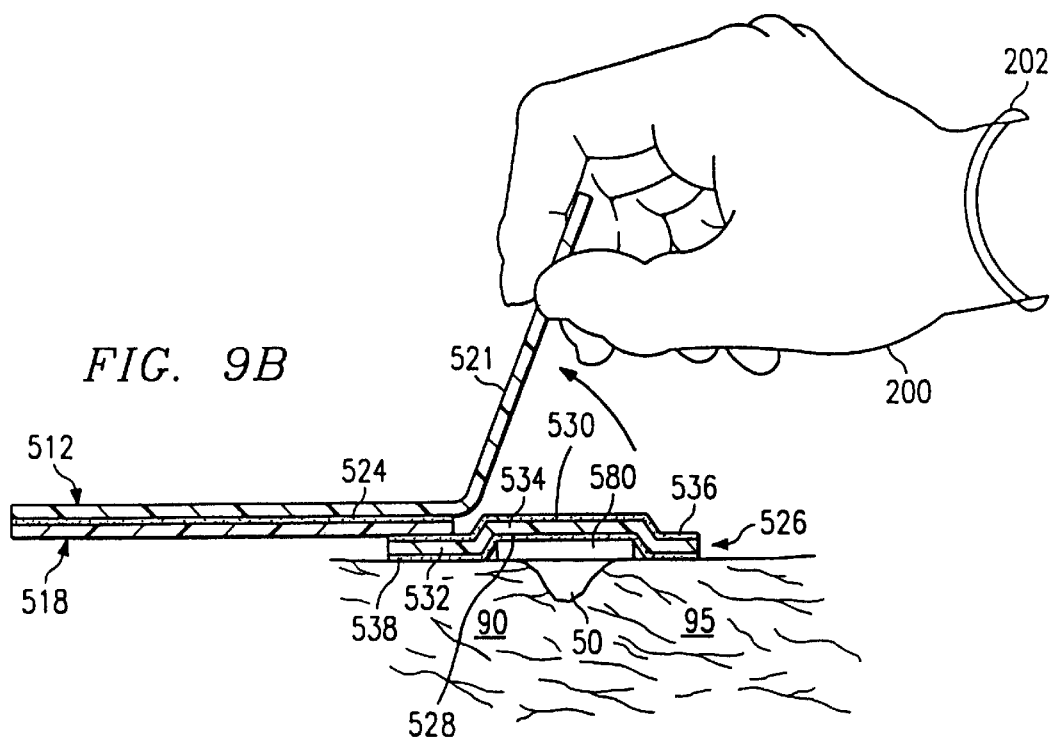
Figure 9C:
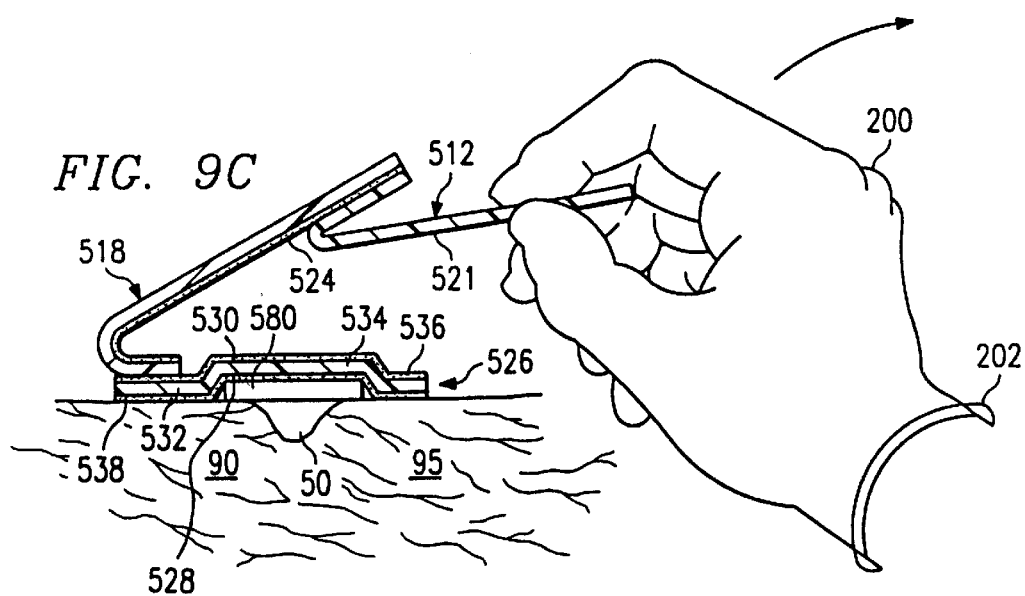
Figure 9D:
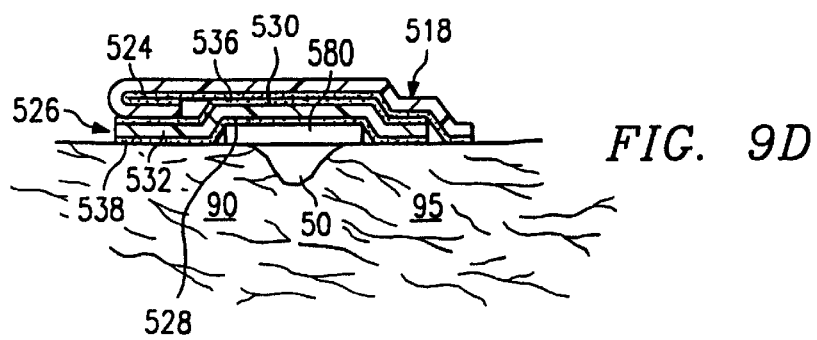

Once hinge member 26 has been affixed to the patient's skin adjacent to wound 50, care giver 200 may grasp handle member 512 at an area remote from cover member 518, and peel handle member 512 away from hinge member 526 until cover dressing 518 is encountered (FIG. 9B). Upon encountering cover dressing 518, care giver 200 peels handle member 512 away from cover dressing 518, drawing cover dressing 518 over wound 50 and primary dressing 580 (FIG. 9C) . Care giver 200 continues to peel handle member 512 from cover dressing 518 until cover dressing 518 overlies primary dressing 580 and handle member 512 separates from cover dressing 518. Care giver 200 may write notes or sketch on handle member 512, and retain handle member 512 in the patient's records for future reference. Once cover dressing 518 is disposed in an overlying relationship to primary dressing 580, care giver 200 may apply pressure to cover member 518 to affix cover member 518 securely to the skin surrounding wound 50 (FIG. 9D). Cover member 518 forms a barrier around primary dressing 580 and wound 50. This barrier may prevent external contaminants from entering the wound site, and may also prevent wound exudates from leaking from the wound site.

Although the present invention and its advantages have been described in detail, it should be understood that various changes, substitutions, and alterations can be made therein without departing from the spirit and scope of the invention as defined in the following claims.

What is claimed is:

1. A wound covering device for covering and sealing at least a portion of a patient's wound comprising:

an elongated handle member having a first side and a second side, the handle member being operable to facilitate alignment of the wound covering device adjacent to the wound to be covered;

a cover dressing having a first side and a second side, the second side of the cover dressing being releasably secured to the first side of the handle member;

a first adhesive layer on at least a portion of the second side of the cover dressing disposed between the second side of the cover dressing and the first side of the handle member, the first adhesive layer operable to secure the second side of the cover dressing to the patient's skin adjacent to the wound when the cover dressing is disposed in overlying relation to the wound;

the first adhesive layer releasably securing the first side of the handle member with the second side of the cover dressing;

a flexible hinge member having a first side and a second side, the flexible hinge member also having a width that is approximately coextensive with a portion of the wound to be covered by the wound covering device, the hinge member further having a first portion disposed on the first side of the cover dressing and a second portion disposed on the first side of the handle member;

a second adhesive layer disposed between the second side of the first portion of the hinge member and the first side of the cover dressing for securing the first portion of the hinge member to the first side of the cover dressing; and a third adhesive layer disposed on at least a portion of the first side of the hinge member for securing the first side of the hinge member to the patient's skin adjacent to the wound.

2. The wound covering device of claim 1, wherein the cover dressing comprises a substantially transparent cover member.

3. The wound covering device of claim 1, further comprising:

the handle member formed from a material selected from the group consisting of paper, polyester, polyethylene and laminates of these materials;

the hinge member formed from a material selected from the group consisting of polyethylene, polyurethane, polyester, woven substrates, non-woven substrates, hydrogel and foam; and the cover dressing formed from a material selected from the group consisting of polyethylene, polyurethane, polypropylene, polyester, woven substrates, non-woven substrates and hydrogel.

4. The wound covering device of claim 1, wherein the first adhesive layer comprises a medicinal agent for assisting in healing the wound.

5. The wound covering device of claim 1, wherein the third adhesive layer comprises a medicinal agent for assisting in healing the wound.

6. The wound covering device of claim 1, wherein the cover dressing comprises a medicinal agent for assisting in healing the wound.

7. The wound covering device of claim 1, wherein the flexible hinge member comprises a medicinal agent for assisting in healing the wound.

8. The wound covering device of claim 1, further comprising a protective member releasably secured to the first side of the hinge member, the protective member being at least coextensive with the third adhesive layer and having a release coating thereon so that the protective member can be readily removed from the hinge member when the wound covering device is to be applied to the patient's skin adjacent to the wound.

9. The wound covering device of claim 8, wherein the protective member has dimensions that are different from the dimensions of the handle member so that the protective member can be readily removed from the hinge member when the device is to be applied to the patient's skin adjacent to the wound.

10. The wound covering device of claim 1, wherein the handle member includes a viewing portion for facilitating alignment of the handle member over at least a portion of the wound to be covered.

11. The wound covering device of claim 1, wherein the handle member includes an alignment pattern for facilitating alignment of the handle member over at least a portion of the wound to be covered.

12. The wound covering device of claim 1, further comprising a primary dressing disposed on the first side of the second portion of the hinge member, for contact with the patient's skin and wound.

13. The wound covering device of claim 12, wherein the primary dressing comprises a material selected from the group consisting of foam, hydrogel, hydrocolloid, silicon, woven substrates, non-woven substrates and alginate, and wherein the primary dressing is hydrophobic.

14. The wound covering device of claim 12, wherein the primary dressing comprises a material selected from the group consisting of foam, hydrogel, hydrocolloid, silicon, woven substrates, non-woven substrates and alginate, and wherein the primary dressing is hydrophilic.

15. The wound covering device of claim 12, wherein the primary dressing comprises a medicinal agent for assisting in healing the wound.

16. The wound covering device of claim 12, wherein the primary dressing comprises a first fenestration, and wherein the hinge member comprises a second fenestration corresponding to the first fenestration in the primary dressing, the first and second fenestrations operating to facilitate alignment and securement of the wound covering device over a device extending from the patient's skin.

17. The wound covering device of claim 12, wherein a portion of the perimeter of the primary dressing and a portion of the perimeter of the hinge member are excised to form a dry edge on the handle member around a portion of the perimeter of the primary dressing and a portion of the perimeter of the hinge member.

18. A method of covering and sealing a wound in a patient using a wound covering device and a primary dressing comprising the steps of:

aligning the wound covering device adjacent to the wound;

applying the primary dressing to a portion of the wound to be covered;

applying pressure to a flexible hinge member of the wound covering device adjacent to the wound to cause the flexible hinge member to adhere to the patient's skin adjacent the wound;

grasping a handle member of the wound covering device at a portion of the handle member that is remote from a cover dressing of the wound covering device;

peeling the handle member away from the hinge member until the cover dressing is encountered;

peeling the handle member away from the cover dressing to draw the cover dressing over the primary dressing and the portion of the wound to be covered;

covering the primary dressing and the portion of the wound to be covered with the cover dressing; and forming a barrier around the perimeter of the portion of the wound to be covered.

19. The method of claim 18, wherein the step of aligning the wound covering device comprises the step of aligning the wound covering device according to an alignment pattern on the handle member.

20. The method of claim 18, wherein the step of applying the primary dressing comprises the step of aligning a first fenestration in the primary dressing and a second fenestration the hinge member with a medical device extending from the patient's skin so that the medical device extends through the respective first and second fenestrations in the primary dressing and the hinge member.

21. The method of claim 18, further comprising the step of securing the primary dressing to a portion of the hinge member extending from the cover dressing.

22. A method of aligning a wound covering device adjacent to a patient's wound comprising the steps of:

aligning a portion of the wound to be covered within a viewing portion of a handle member of the wound covering device;

applying pressure to a flexible hinge member of the wound covering device adjacent to the wound to cause the flexible hinge member to adhere to the patient's skin adjacent the wound;

grasping the handle member of the wound covering device at a portion of the handle member that is remote from a cover dressing of the wound covering device;

peeling the handle member away from the hinge member until the cover dressing is encountered;

peeling the handle member away from the cover dressing to draw the cover dressing over the portion of the wound to be covered;

covering the portion of the wound to be covered with the cover dressing; and forming a barrier around the perimeter of the portion of the wound to be covered.

23. The method of claim 22, wherein the step of aligning the wound covering device comprises the step of aligning the wound covering device according to an alignment pattern on the handle member.

24. The method of claim 22, wherein the step of aligning the wound covering device comprises the step of aligning an alignment pattern on the handle member with a medical device extending from the patient's skin.

25. The method of claim 22, further comprising the steps of:

sketching the perimeter of the wound on the handle member; and retaining the handle member for reference.

26. A wound covering device for sealing and covering at least a portion of a patient's wound, comprising:

an elongated handle member configured for aligning and applying said wound covering device to the patient;

a cover dressing having a wound covering side releasably attached to said handle member, said wound covering side configured for placement against the patient's skin for covering the wound;

a hinge member attached at one end thereof to said cover dressing and having a first side with an adhesive thereon for securing said first side to the patient's skin at least in an area adjacent the wound, said first side facing opposite from said wound covering side of said cover dressing, said hinge member having a second side releasably attached to said handle member on the same side thereof as said wound covering side of said cover dressing; and wherein once said first side of said hinge member is pressed against a patient's skin adjacent to the wound, said handle member is used to pull and fold said cover dressing over said hinge member to press said wound covering side thereof to the patient's skin whereby said cover dressing covers the wound and is held against the skin surrounding the wound.

27. The wound covering device as in claim 26, further comprising an adhesive disposed on said wound covering side of said cover dressing for adhering said wound covering side to the patient's skin, said handle member releasably secured to said adhesive.

28. The wound covering device as in claim 27, further comprising an adhesive on said second side of said hinge member, said handle member releasably secured to said adhesive on said second side of said hinge member.

29. The wound covering device as in claim 28, wherein said adhesive on said wound covering side of said cover dressing folds onto said adhesive on said second side of said hinge member.

30. The wound covering device as in claim 26, wherein said first side of said hinge member has a length so as to be adhered to the patient's skin adjacent to but not to extend over the wound.

31. The wound covering device as in claim 26, wherein said first side of said hinge member has a length so as to be adhered to the patient's skin adjacent to the wound and to extend over the wound, said cover dressing thereby covering the wound and at least a portion of said hinge member extending over the wound.

32. The wound covering device as in claim 26, wherein said cover dressing comprises a substantially transparent material.

33. The wound covering device as in claim 26, wherein at least a portion of said second side of said hinge member overlies said cover dressing wherein said hinge member is attached to said cover dressing.

34. The wound covering device as in claim 33, further comprising an adhesive disposed between said portion of said hinge member overlying said cover dressing and said cover dressing.

35. The wound covering device as in claim 26, wherein said cover dressing comprises a medicinal agent for assisting in healing the wound.

36. The wound covering device as in claim 26, wherein said hinge member comprises a medicinal agent for assisting in healing the wound.

37. The wound covering device as in claim 26, further comprising a protective member releasably secured to at least said first side of said hinge member.

38. The wound covering device as in claim 26, further comprising a primary dressing disposed on said first side of said hinge member, said hinge member and primary dressing having a length and width so as to cover at least a portion of the wound when said first side of said hinge member is pressed against the patient's skin.

39. The wound covering device as in claim 38, wherein said primary dressing comprises a medicinal agent for assisting in healing the wound.

* * * * *

UNITED STATES PATENT AND TRADEMARK OFFICE
CERTIFICATE OF CORRECTION

PATENT NO. : 5,960,795
DATED : October 5, 1999
INVENTOR(S) : Tod H. Shultz

It is certified that error appears in the above-identified patent and that said Letters Patent is hereby corrected as shown below:

On the title page: Item [75] change the inventor's name from "Schultz" to "Shultz"

Signed and Sealed this

Fifth Day of September, 2000

Attest:

Q. TODD DICKINSON

Attesting Officer

Director of Patents and Trademarks